United States Patent [19]

Maruyama et al.

[11] Patent Number: 5,560,930
[45] Date of Patent: Oct. 1, 1996

[54] METHOD FOR PREPARING AQUEOUS EMULSION FOR COATING SOLID PHARMACEUTICAL PREPARATIONS

[75] Inventors: Naosuke Maruyama; Hiroyasu Kokubo, both of Nakakubiki-gun; Yoshiaki Kawashima, Gifu, all of Japan

[73] Assignee: Shin-Etsu Chemical Co., Ltd., Japan

[21] Appl. No.: 360,649

[22] Filed: Dec. 21, 1994

[30] Foreign Application Priority Data

Dec. 27, 1993 [JP] Japan .................... 5-331431
Dec. 27, 1993 [JP] Japan .................... 5-331432

[51] Int. Cl.$^6$ ..................................... A61K 9/14
[52] U.S. Cl. .................... 424/488; 424/489; 424/490; 424/468
[58] Field of Search .............. 514/165; 424/488, 424/489, 490, 468

[56] References Cited

U.S. PATENT DOCUMENTS 3,615,792 10/1971 Keene ..................... 106/170
5,025,004 6/1991 Wu et al. ................. 514/165
5,126,146 6/1992 Seminoff ................. 424/468

OTHER PUBLICATIONS

"Porosity–Controlled Ethylcellulose Film Coating, I. Formation of Porous Ethylcellulose Film in the Casting Process and Factors Affecting Film–Density" by Shinji Narisawa et al., Feb. 1993, Chemical & Pharmaceutical Bulletin 41 (1993) Feb., No. 2, Tokyo, Japan, pp. 329–334.

*Primary Examiner*—Thurman K. Page
*Assistant Examiner*—William E. Benston, Jr.
*Attorney, Agent, or Firm*—Parkhurst, Wendel & Burr, L.L.P.

[57] ABSTRACT

A method permits the easy preparation of an aqueous emulsion for coating solid pharmaceutical preparations through emulsification in water without addition of additives such as emulsifying agents, polymerization initiators, chain transfer agents, salts and plasticizers. A cellulosic polymer is dissolved in an organic solvent miscible in water in any rate or a mixed solvent comprising the organic solvent and water to give a polymer solution. The polymer solution is mixed with water to disperse the solution in water and thereafter the organic solvent is removed to form an aqueous emulsion for coating solid pharmaceutical preparations. If ethyl cellulose is used as a coating base, ethyl cellulose is first dissolved in a non-hydrophilic solvent to give a non-hydrophilic solution thereof. The non-hydrophilic solution is dissolved in a solvent containing at least an organic solvent miscible with water in any rate, the resulting ethyl cellulose solution is brought into contact with water to disperse the ethyl cellulose solution therein and then the solvent is removed from the emulsion formed through self-emulsification of the ethyl cellulose solution to form an aqueous coating emulsion.

3 Claims, No Drawings

METHOD FOR PREPARING AQUEOUS EMULSION FOR COATING SOLID PHARMACEUTICAL PREPARATIONS

BACKGROUND OF THE INVENTION

The present invention relates to a method for preparing an aqueous emulsion for use in coating a medicine, in particular, an enteric solid pharmaceutical preparation.

In the solid pharmaceutical preparation provided with an enteric coating, the enteric coating serves to not only protect drugs having low resistance to acids from the attack thereof in the stomach, but also protect the gastric mucous membrane from the attack of drugs which may stimulate and damage the wall of the stomach and is dissolved after the arrival at the intestines in which the pharmaceutical preparation shows its desired pharmacological action. There have been used acrylic polymers and cellulosic polymers as enteric coating bases. The acrylic polymer may be, for instance, a copolymer of methacrylic acid and ethyl acrylate. Examples of such cellulosic polymers are cellulose acetate phthalate, hydroxypropyl-methyl cellulose phthalate, hydroxypropylmethyl cellulose acetate succinate, cellulose acetate trimellitate, and carboxymethylethyl cellulose. These coating bases are used in the coating treatment of pharmaceutical preparations in the form of a solution in an organic solvent or an aqueous latex or an aqueous dispersion.

Ethyl cellulose has widely been used as a coating base for solid pharmaceutical preparations such as tablets and granules. Ethyl cellulose is prepared by reacting linter pulp or wood pulp as a raw material with an etherifying agent. In ethyl cellulose, 45 to 50% of the hydroxyl groups present therein are replaced with ethoxy groups and therefore, ethyl cellulose has hydrophobicity and thus exhibits excellent film-forming properties. Ethyl cellulose has been used in the field of drugs and, more specifically, it is used, as an agent for masking a bitter taste of a drug, in a coating film for sustained release pharmaceutical preparations or the like, while making the most use of properties of these ethoxy groups. When practicing the coating procedures using ethyl cellulose, the cellulose is first dissolved in an organic solvent and then applied to solid pharmaceutical preparations.

Recently, the use of organic solvents has been regulated due to the problem of environmental pollution and accordingly, coating treatments which make use of aqueous systems have widely been adopted.

There have already been proposed a variety of coating techniques which make use of aqueous systems. For instance, Japanese Patent Application Publication No. 60-43334 discloses a coating emulsion of an acrylic polymer. The acrylic polymer is a copolymer obtained through emulsion polymerization of methacrylic acid and ethyl acrylate and stably dispersed in the coating emulsion in the form of particles having a particle size of not more than 1µm. However, the coating emulsion comprises residual emulsifying agent, polymerization initiator, chain transfer agent, unreacted monomers or the like and is not preferred as an ingredient of solid pharmaceutical preparations from the viewpoint of safety.

In addition, there has also been proposed a method for preparing an aqueous coating system which comprises dispersing a cellulosic polymer in water. Examples of methods for dispersing a cellulosic polymer in water include a method comprising adding salts together with the polymer or neutralizing the carboxyl groups of the polymer and a method comprising dispersing, in water, the cellulosic polymer in the form of fine particles thereof.

With regard to the former method, Japanese Patent Application Publication No. 61-56221 discloses a method comprising the steps of emulsifying cellulose acetate phthalate, then adding a phosphoric acid salt as an antiflocculant and spray-drying the resulting emulsion to give a powdery polymer capable of being redispersed in water. The emulsification of cellulose acetate phthalate is carried out according to the method as disclosed in U.S. Pat. No. 4,177,177. Moreover, Japanese Patent Provisional Publication No. 56-30913 discloses a method in which cellulose acetate phthalate or hydroxypropylmethyl cellulose phthalate is used in coating procedures in the form of an aqueous solution of the cellulose derivative neutralized with ammonia. In addition, Japanese Patent Provisional Publication No. 58-135807 discloses a method which comprises the steps of neutralizing a cellulosic polymer with an alkali, then dissolving it in water and adding a carboxylic acid to the resulting solution. All of the films for coating solid enteric pharmaceutical preparations formed according to these methods comprise residual alkali salts or ammonium salts of the carboxylic acids used. For this reason, the quality of the resulting coated solid pharmaceutical preparations would be deteriorated or impaired because of high hygroscopicity of these alkali or ammonium salts remaining in the coating film.

With regard to the latter method, Japanese Patent Application Publication No. 56-12614 discloses a method comprising dispersing a cellulosic polymer having an average particle size of not more than 100 µm in water which comprises a gelling agent (plasticizer) and has a boiling point of not less than 100° C. Moreover, Japanese Patent Application Publication Nos. 57-53329 and 58-55125 disclose that triacetin ortriethyl citrate is used as a gelling agent. When mechanically pulverizing a polymer derivative to disperse the polymer, the particle size of the resulting powdery polymer is at least not less than 1 µm. The use of a plasticizer is indispensable to the dispersion of such a polymer having a particle size of not less than 1µm, the polymer is softened through heating and precipitated in the dispersion through flocculation.

Alternatively, Japanese Patent Provisional Publication No. 63-192725 discloses a method which comprises dispersing ethyl cellulose having an average particle size of not more than 100 µm together with a water-soluble plasticizer to give a sustained release film-forming agent, as a technique for coating solid pharmaceutical preparations.

In these dispersions for use in such a coating treatment, the polymer should have a particle size of at least not less than 1µm since the polymer is mechanically pulverized. In this case, the use of a plasticizer is likewise indispensable to the dispersion of a polymer having a particle size of not less than 1µm, the polymer is softened through heating and precipitated in the dispersion through flocculation. Moreover, the dispersion, i.e., the sustained release film-forming agent, prepared according to this method must be coated in a substantial amount to ensure the formation of a film having sustained release properties.

Japanese Patent Application Publication No. 3-39490 discloses a method for eliminating the drawbacks associated with the coating technique which makes use of the aqueous cellulose system, by reducing the particle size of a cellulosic polymer dispersed in water through emulsification. The emulsification is carried out according to the method as disclosed in U.S. Pat. No. 4,177,177. More specifically, the cellulosic polymer is dissolved in a water-immiscible organic solvent to give a polymer solution. A hydrocarbon having not less than 8 carbon atoms (such as cetyl alcohol) and a surfactant as stabilizers are added to the polymer solution and then the resulting polymer solution is treated by a particular emulsifier such as a high pressure homogenizer to give an emulsion. As has been discussed above in detail, the conventional aqueous coating solutions comprise components other than the cellulosic polymers such as stabilizers and surfactants. These stabilizers and surfactants often impair the resistance to acid and stability of the resulting coated solid pharmaceutical preparations. For this reason, there has been desired for the development of a coating solution having a simple composition as much as possible.

SUMMARY OF THE INVENTION

An object of the present invention is generally to solve the foregoing problems and more specifically to provide a method which permits the easy preparation of an aqueous emulsion for coating solid pharmaceutical preparations through emulsification in water without addition of additives such as emulsifying agents, polymerization initiators, chain transfer agents, salts and plasticizers conventionally used.

According to the present invention, the foregoing object of the present invention can effectively be accomplished by providing a method for preparing an aqueous emulsion for coating a solid pharmaceutical preparation, which comprises the steps of dissolving a cellulosic polymer in an organic solvent miscible with water in any rate, or a mixed solvent comprising the solvent and water, or a mixed solvent comprising the solvent and non-hydrophilic solvent, or a mixed solvent comprising the solvent and water; and then bringing the resulting polymer solution into contact with water to disperse the polymer solution therein, and then removing the solvent from the emulsion formed through self-emulsification of the polymer solution.

DETAILED DESCRIPTION OF THE INVENTION

Cellulosic polymers may serve as bases for coating solid pharmaceutical preparations. Examples of cellulosic polymers usable herein include polymers commonly used in the organic solvent type coating solutions, such as hydroxypropylmethyl cellulose phthalate, hydroxypropylmethyl cellulose acetate succinate, cellulose acetate phthalate, cellulose acetate trimellitate, carboxymethyl ethyl cellulose, and ethyl cellulose. These cellulosic polymers may be used alone or in any combination thereof.

Examples of organic solvents usable in the present invention are those miscible with water in any rate such as alcohols, e.g., methanol, ethanol and isopropanol; and ketones, e.g., acetone and methyl ethyl ketone. Appropriate amount of hydrophobic solvent may be added. These organic solvents may likewise be used alone or in any combination. Also, a small amount of non-hydrophilic solvents may be used. Preferred are those having a low boiling point since they can easily be removed after emulsification.

The mixed solvent of an organic solvent and water must have a composition which ensures the complete dissolution of the cellulosic polymers. The content of water in the mixed solvent varies depending on the kinds of cellulosic polymers selected, but is in general not more than 60% by weight.

The polymer concentration of the polymer solution preferably is less than 10% by weight, more preferably from 2 to 10 % by weight. This is because, if the concentration is not less than 10% by weight, the viscosity of the resulting polymer solution is too high to emulsify the solution in the form of fine particles having a particle size of not more than 1 µm. If it is not more than 2 % by weight, the concentration of the aqueous emulsion finally obtained is too low, therefore productivity is decreased.

The amount of water to be admixed with the polymer solution preferably is at least 80 % by weight, more preferably from 80 to 150 % by weight on the basis of the weight of the polymer solution. This is because, if it is not more than 80% by weight, the solvent insufficiently diffuses from the solution to water and this results in incomplete emulsification. If it is not less than 150 % by weight, the concentration of the aqueous emulsion finally obtained is too low; therefore it needs to be concentrated.

The emulsification process comprises the steps of dissolving a cellulosic polymer in an organic solvent or the foregoing mixed solvent to give a polymer solution and then mixing the resulting polymer solution with water in a predetermined rate. The solution and/or the mixture with water may gently and continuously be stirred with a usual stirring device during the emulsification process, but the strength of the stirring does not affect the quality of the resulting emulsion. However, if the stirring speed is too slow, the organic solvent in the polymer solution does not sufficiently diffuse from the polymer solution to the water phase and accordingly, an emulsion comprising particles having a particle size of not more than 1 µm cannot be obtained. Thereafter, the organic solvent is removed by distillation or distillation under reduced pressure according to the usual method to give an aqueous emulsion for coating solid pharmaceutical preparations. Surfactants may be added for stabilization of emulsion, and for other purposes.

The coating treatment comprises the steps of spraying solid enteric pharmaceutical preparations with a coating solution using a coating device and then drying the sprayed solution on the preparations to form a film thereon. The coating solution comprises the aqueous emulsion prepared above to which is added a pharmaceutically acceptable plasticizer such as triethyl citrate and/or triacetin. Examples of coating devices usable herein are a fluidized bed coating device, a pan-coating device and a vented rotary drum type coating device. Solid pharmaceutical preparations are sprayed with the coating solution using these devices and then the water in the solution is vaporized by feeding warmed air thereto to thus form a coating film for the solid pharmaceutical preparations.

Ethyl cellulose may be any presently commercially available one and serves as a base for coating solid pharmaceutical preparations. Specific examples thereof include Shin-Etsu Cellulose N-7-G, N-7-F, N-10-G and N-10-F (available from Shin-Etsu Chemical Co., Ltd.). If these ethyl cellulose products are dissolved in a toluene/ethanol mixed solvent having a toluene content of 80% by weight to an ethyl cellulose concentration of 5% by weight, the resulting solutions have viscosities of 7 cp and 10 cp respectively.

The resulting emulsion has a low ethyl cellulose concentration and therefore, the emulsion as such cannot be used as a coating solution. The ethyl cellulose concentration of the coating solution is preferably not less than 7% by weight and accordingly, it is necessary to concentrate the emulsion. The emulsion can be concentrated to a high concentration by an ultrafiltration membrane rather than a heating device such as a vacuum distillation device in which a high expense is required for steaming, within a short period of time. A porous membrane whose fractional molecular weight is 50,000 or 200,000 is employed to give a coating solution containing ethyl cellulose having a molecular weight ranging from 100,000 to 1,000,000. Examples of materials for the porous membranes are polysulfone, polyvinylidene fluoride, cellulose acetate and ceramics. Examples of ultrafiltration modules usable herein include flat sheet, tubular, spiral and hollow fiber type ones.

The coating treatment comprises the steps of spraying solid enteric pharmaceutical preparations with the coating solution using a coating device and then drying the sprayed solution to form a film thereon. A specific coating treatment is identical to that already described above.

The method for preparing an aqueous coating emulsion according to the present invention permits easy emulsification, in water, of a coating base through dissolution of the base in an organic solvent having a specific composition without addition of additives such as salts, plasticizers and emulsifying agents (surfactants). The resulting emulsion is stable to heat. Therefore, it can withstand the distillation procedures for removing the solvent without causing any flocculation through heating. Moreover, substances harmful to human bodies are also removed during the removal of the solvent. The emulsion can be used to coat solid pharmaceutical preparations to thus give coated preparations having excellent resistance to acids and high stability.

The present invention will hereunder be explained in more detail with reference to the following Examples, but the present invention is by no means limited to these specific Examples.

First of all, an aqueous emulsion for coating solid enteric pharmaceutical preparations will be detailed below.

EXAMPLE 1

A polymer solution was prepared by dissolving 0.3 kg of hydroxypropylmethyl cellulose phthalate (HP-55 available from Shin-Etsu Chemical Co., Ltd.) in 9.7 kg of acetone. The polymer solution was emulsified by pouring the solution into 10 kg of water at a rate of 1 kg/sec while stirring the solution at 100 rpm. The resulting emulsion was subjected to vacuum distillation at a jacket temperature of 50° C. and a degree of vacuum of −590 mmHg using an evaporator to eliminate the solvent. Then the emulsion was further concentrated at a jacket temperature of 60° C. and a degree of vacuum of −730 mmHg. The resulting concentrate was passed through a 200 mesh sieve to remove the agglomerates present therein. The content of the agglomerates in the concentrate was found to be 0.1% by weight and the polymer concentration thereof was 10% by weight. The average particle size of the polymer present in the emulsion thus prepared was found to be 0.2 μm.

Triethyl citrate as a plasticizer was added to the emulsion in an amount of 15% by weight on the basis of the amount of the polymer, like the practical coating followed by casting the mixture on a glass plate to form a continuous transparent film. The resulting film was inspected for the disintegration according to the test for enteric pharmaceutical preparations as defined by the disintegration test method disclosed in the Japanese Pharmacopoeia. More specifically, the film was immersed in a first solution having a pH of 1.2 (artificial gastric juice) for 2 hours while maintaining the first solution at 37° C. (body temperature). As a result, the film did not cause any change at all even after 2 hours.

COMPARATIVE EXAMPLE 1

Emulsification was carried out according to the same procedures used in Example 1 except that the amount of water which was poured into the polymer solution was changed to 5000 g. As a result, it was found that the diffusion of the solvent from the polymer solution to water was insufficient, that the polymer solution was separated into two phases and that a part of the polymer was converted into gel-like precipitates.

COMPARATIVE EXAMPLE 2

Emulsification was carried out according to the same procedures used in Example 1 except that the amount of hydroxypropylmethyl cellulose phthalate was changed to 1.2 kg. As a result, it was found that the diffusion of the solvent from the polymer solution to water was insufficient, that the polymer solution was separated into two phases and that a part of the polymer was converted into gel-like precipitates.

EXAMPLE 2

A polymer solution was prepared by dissolving 50 g of hydroxypropylmethyl cellulose phthalate (HP-55 available from Shin-Etsu Chemical Co., Ltd.) in 950 g of a mixed solvent of ethanol and water (ethanol/water (weight ratio)= 8/2). The polymer solution was emulsified by pouring 1000 g of water into the solution at a rate of 200 g/sec while stirring the water at 100 rpm. The resulting emulsion was subjected to vacuum distillation at a jacket temperature of 60° C. and a degree of vacuum of −545 mmHg using an evaporator to eliminate the solvent. Then the concentrate was passed through a 200 mesh sieve to remove the agglomerates therefrom. The content of the agglomerates in the concentrate was found to be 0.3% by weight and the polymer concentration thereof was 6% by weight. The average particle size of the polymer present in the emulsion thus prepared was found to be 0.2μm.

Triethyl citrate as a plasticizer was added to the emulsion so that the concentration thereof was equal to 15% by weight on the basis of the amount of the polymer, like the practical coating followed by casting the mixture on a glass plate to form a continuous transparent film. The resulting film was immersed in a first solution having a pH of 1.2 for 2 hours according to the test for enteric pharmaceutical preparations as defined by the disintegration test method disclosed in the Japanese Pharmacopoeia. As a result, the film did not cause any change at all even after 2 hours.

EXAMPLE 3

A polymer solution was prepared by dissolving 50 g of hydroxypropylmethyl cellulose acetate succinate (Shin-Etsu AQOAT AS-MF available from Shin-Etsu Chemical Co., Ltd.) in 950 g of a mixed solvent of methanol and water (methanol/water (weight ratio)=8/2). The polymer solution was emulsified by pouring the solution into 1000 g of water. The resulting emulsion was subjected to vacuum distillation at a jacket temperature of 50° C. and a degree of vacuum of −490mmHg using an evaporator to eliminate the solvent. Then the concentrate was passed through a 200 mesh sieve to remove the agglomerates present therein. The content of the agglomerates in the concentrate was found to be 0.5% by weight and the polymer concentration thereof was 4% by weight. The average particle size of the polymer present in the emulsion thus prepared was found to be 0.3μm. A film of the emulsion was prepared by the same method used in Example 1 and subjected to a disintegration test. As a result, it was found that the film did not undergo any change.

EXAMPLE 4

Emulsification was carried out in the same manner used in Example 2 except that the amount of water which was poured into the polymer solution was changed to 850 g. It was found that the content of the agglomerates present in the resulting concentrate was 2.1% by weight and that the polymer concentration thereof was 5% by weight. The average particle size of the polymer present in the resulting emulsion was found to be 0.3μm. A film of the emulsion was prepared by the same method used in Example 1 and subjected to a disintegration test. As a result, it was found that the film did not undergo any change.

EXAMPLE 5

Emulsification was carried out in the same manner used in Example 2 except that the amount of water in the mixed solvent (950 g) was changed to 30% by weight. It was found that the content of the agglomerates present in the resulting concentrate was 3.3% by weight and that the polymer concentration thereof was 6% by weight. The average particle size of the polymer present in the resulting emulsion was found to be 0.2μm. A film of the emulsion was prepared by the same method used in Example 1 and subjected to a disintegration test. As a result, it was found that the film did not undergo any change.

EXAMPLE 6

Emulsification was carried out in the same manner used in Example 2 except that the amount of the hydroxypropylmethyl cellulose phthalate (HP-55) was changed to 70 g. It was found that the content of the agglomerates present in the resulting concentrate was 5.7% by weight and that the polymer concentration thereof was 7% by weight. The average particle size of the polymer present in the resulting emulsion was found to be 0.3μm. A film of the emulsion was prepared by the same method used in Example 1 and subjected to a disintegration test. As a result, it was found that the film did not undergo any change.

EXAMPLE 7

Emulsification was carried out in the same manner used in Example 1 except that the amount of the hydroxypropylmethyl cellulose phthalate (HP-55) was changed to 50 g. As a result, the content of the agglomerates present in the resulting concentrate was found to be 0.3% by weight and the polymer concentration thereof was about 6% by weight. The average particle size of the polymer present in the resulting emulsion was found to be 0.2μm. a film of the emulsion was prepared by the same method used in Example 1 and subjected to a disintegration test. As a result, it was found that the film did not undergo any change.

EXAMPLE 8

Emulsification was carried out in the same manner used in Example 1 except that 50g of carboxymethyl ethyl cellulose (CMEC AQ available from Freunt Sangyo K.K.) was used as a cellulosic polymer. It was found that the content of the agglomerates present in the concentrate was 0.3% by weight and that the polymer concentration thereof was about 6% by weight. The average particle size of the polymer present in the resulting emulsion was found to be 0.4 μm. A film of the emulsion was prepared by the same method used in Example 1 and subjected to a disintegration test. As a result, it was found that the film did not undergo any change.

EXAMPLE 9

To the emulsion prepared in Example 1, there was added, as a plasticizer, triethyl citrate in an amount of 35% by weight on the basis of the weight of the hydroxypropylmethyl cellulose phthalate to give a coating solution.

Pillar-shaped pancreatin granules having a diameter of 0.8 mm were sprayed with the coating solution. The spraying operation was performed using a coating device: FLOW-COATER FLO-1 (available from Freunt Sangyo K.K.). The spray speed during the spraying operation was set at 60 g/min. After the spraying process, hot air of 80 T was fed to the pancreatin granules having a temperature of 33° C. at a flow rate of 2.7 m$^3$/min to evaporate the moisture present on the surface thereof at an exhaust gas temperature of 37° C. Thus, there were prepared 5 groups of pillar-shaped pancreatin granules different from each other in the weights of the coating films which ranged from 10 to 18% by weight.

The amount of pancreatin dissolved and released into the gastric juice as the result of disintegration of the enteric coating film of the pancreatin granules was determined according to the test for the enteric pharmaceutical preparations as defined by the disintegration test disclosed in Japanese Pharmacopoeia-12 using a dissolution tester. More specifically, the coated pancreatin granules were immersed in a first solution having a pH of 1.2 (artificial gastric juice) for 2 hours while maintaining the first solution at 37° C. (body temperature) and then the amount of pancreatin released from the granules was determined. The results thus obtained are listed in the following Table 1.

COMPARATIVE EXAMPLE 3

Hydroxypropylmethyl cellulose phthalate (HP-55F) having an average particle size of 8 μm was dispersed in water and the resulting solution was used as a plasticizer. Triethyl citrate was added to the plasticizer in an amount of 35% by weight on the basis of the weight of HP-55F to give a coating solution.

The coating was performed in the same manner used in Example 9. Thus, there were prepared 5 groups of pillar-shaped pancreatin granules different from each other in the weights of the coating films which ranged from 14 to 25% by weight. The coated pancreatin granules were immersed in a first solution (pH 1.2) for 2 hours and then the amount of pancreatin released from the granules was determined according to the test for the enteric pharmaceutical preparations as defined by the disintegration test disclosed in Japanese Pharmacopoeia-12. The results thus obtained are listed in the following Table 1.

COMPARATIVE EXAMPLE 4

Hydroxypropylmethyl cellulose phthalate (HP-55UF) having an average particle size of 5μm was dispersed in water and the resulting solution was used as a plasticizer. Triethyl citrate was added to the plasticizer in an amount of 35% by weight on the basis of the weight of HP-55UF to give a coating solution.

The coating was performed in the same manner used in Example 9. Thus, there were prepared 5 groups of pillar-shaped pancreatin granules different from each other in the weights of the coating films which ranged from 12 to by weight. The coated pancreatin granules were immersed in a first solution (pH 1.2) for 2 hours and then the amount of pancreatin released from the granules was determined according to the test for the enteric pharmaceutical preparations as defined by the disintegration test disclosed in Japanese Pharmacopoeia-12. The results thus obtained are listed in the following Table 1.

TABLE 1

| Amount of Film (% by weight) | Release Rate of Pancreatin After 2 Hr. (% by weight) | | |
|---|---|---|---|
| | Example 9 | Comp. Example 3 | Comp. Example 4 |
| 10 | 29.1 | — | — |
| 12 | 11.8 | — | 28.5 |
| 14 | 3.2 | 45.5 | 11.2 |
| 16 | 1.3 | 38.1 | 1.1 |
| 18 | 0.3 | 30.2 | 0.5 |
| 20 | — | 20.0 | 0.4 |
| 25 | — | 9.8 | — |

The data listed in Table 1 clearly indicate that the coating solution of Example 9 exhibits excellent resistance to acids as compared with the coating solutions of Comparative Examples 3 and 4.

EXAMPLE 10

A polymer solution was prepared by dissolving 0.05 kg of hydroxypropylmethyl cellulose phthalate (HP-55) in 4.95 kg of a mixed solvent of ethanol and water (ethanol/water (weight ratio)=8/2). The polymer solution was emulsified by pouring 10 kg of water into the solution at a rate of 2 kg/sec while stirring the water at 100 rpm. The resulting emulsion was eliminated of the solvent and removed of the agglomerates by the same method used in Example 2. The content of the agglomerates in the concentrate was found to be 0.3 % by weight and the polymer concentration thereof was 5 % by weight. The average particle size of the polymer present in the emulsion thus prepared was found to be 0.2μm.

Then an aqueous emulsion for coating solid pharmaceutical preparations, whose coating base is ethyl cellulose, will hereunder be explained in detail.

EXAMPLE 11

An ethyl cellulose solution was prepared by dissolving 0.3 kg of ethyl cellulose (N-10 available from Shin-Etsu Chemical Co., Ltd.) in 9.7 kg of acetone. The ethyl cellulose solution was emulsified by pouring it into 10 kg of water at a rate of 1 kg/sec while stirring the water at 100 rpm. The resulting emulsion was subjected to vacuum distillation at a jacket temperature of 50° C. and a degree of vacuum of −500 mmHg using an evaporator to eliminate the solvent. Then the resulting emulsion was further concentrated at room temperature using an ultrafiltration membrane (flat film module; polysulfone) having a fractional molecular weight of 200,000 and a filtration surface area of 0.65 m$^3$, till the solid content thereof reached 15% by weight. It was found that the membrane had a rate of ethyl cellulose blocking of 100%. The average particle size of the polymer present in the emulsion thus prepared was found to be 0.2 μm.

A continuous film was prepared from the resulting emulsion and the film was inspected for the disintegration properties, in the same manner used in Example 1. As a result, it was found that the film did not cause any change at all even after 2 hours.

COMPARATIVE EXAMPLE 5

Emulsification was performed according to the same procedures used in Example 11 except that the amount of water which was poured into the polymer solution was changed to 5000 g. As a result, it was found that the diffusion of the solvent from the polymer solution to water was insufficient, that the polymer solution was separated into two phases and that a part of the polymer was converted into gel-like precipitates.

EXAMPLE 12

An ethyl cellulose solution was prepared by dissolving 50 g of ethyl cellulose (N-7 available from Shin-Etsu Chemical Co., Ltd.) in 950 g of ethanol. To the ethyl cellulose solution, there was added 1000 g of water at a rate of 200 g/sec while stirring the solution at 100 rpm to emulsify the polymer solution. The resulting emulsion was subjected to vacuum distillation at a jacket temperature of 60° C. and a degree of vacuum of −600 mmHg using an evaporator to eliminate the solvent. Then the resulting emulsion was further concentrated at room temperature using an ultrafiltration membrane (flat film module; polysulfone) having a fractional molecular weight of 200,000 and a filtration surface area of 0.65 m$^3$, till the solid content thereof reached 20% by weight. It was found that the membrane had a rate of ethyl cellulose blocking of 100%. The average particle size of the polymer present in the emulsion thus prepared was found to be 0.3 μm.

A continuous film was prepared from the resulting emulsion and the film was inspected for the disintegration properties, in the same manner used in Example 1. As a result, it was found that the film did not cause any change at all even after 2 hours.

EXAMPLE 13

Emulsification was performed according to the same procedures used in Example 12 except that the amount of water which was poured into the polymer solution was changed to 850 g. The average particle size of the polymer present in the emulsion thus prepared was found to be 0.4μm.

A continuous film was prepared from the resulting emulsion and the film was inspected for the disintegration properties, in the same manner used in Example 1. As a result, it was found that the film did not cause any change at all even after 2 hours.

EXAMPLE 14

To the emulsion prepared in Example 11, there was added, as a plasticizer, triethyl citrate in an amount of 35% by weight on the basis of the weight of the hydroxypropylmethyl cellulose phthalate to give a coating solution.

Placebo tablets of corn starch type lactose having a diameter of 8 mm were sprayed with the coating solution. The spraying operation was performed using a small-sized vented coating device. The spray speed during the spraying operation was set at 10 g/min. After the spraying process, hot air of 70° C. was fed to the placebo tablets of corn starch type lactose having a temperature of 39° C. at an exhaust gas temperature of 36° C. to evaporate the moisture on the surface thereof and to thus give coated tablets.

The disintegration test defined in Japanese Pharmacopoeia-12 was carried out using the placebo tablets of corn starch type lactose (100 tablets). More specifically, the coated tablets were immersed in a first solution having a pH of 1.2 (artificial gastric juice) for 2 hours while maintaining the first solution at 37° C. (body temperature) followed by determination of the number of abnormal tablets and the amount of the first solution penetrated into the tablets. The results thus obtained are listed in the following Table 2.

Comparative Example 6

A test was carried out according to the same procedures used in Example 14 except for the use of Shin-Etsu Cellulose N-7-F (average particle size: 4μm). The results are likewise listed in Table 2.

TABLE 2

| The Amount of Film Applied (% by weight) | 5 | 6 | 10 | 12 |
| --- | --- | --- | --- | --- |
| Example 14 | | | | |
| Rate of Tablets Having Defected | 10 | 0 | 0 | 0 |
| Penetration Rate of 1st Solution | 2.8 | 1.8 | — | — |
| Comp. Ex. 6 | | | | |
| Rate of Tablets Having Defected | — | 89.0 | 34.0 | 0 |
| Penetration Rate of 1st Solution | — | — | 4.2 | 2.4 |

What is claimed is:

1. A method for preparing an aqueous emulsion for coating a solid pharmaceutical preparation comprising the steps of dissolving, in the absence of an emulsifying agent, polymerization initiator, chain transfer agent, salt, or plasticizer, a cellulosic polymer in an organic solvent miscible with water in any amount or a mixed solvent consisting of said organic solvent and water to give a polymer solution having a polymer concentration Of not more than 10% by weight;

mixing the polymer solution with water in an amount of from about 80% to about 150% by weight on the basis of the polymer solution to disperse the solution in water; and then removing the organic solvent to form an aqueous emulsion containing particles having a particle size of no more than 1 μm.

2. The method of claim 1 wherein the organic solvent is at least one member selected from the group consisting of methanol, ethanol, isopropanol, acetone and methyl ethyl ketone and the amount of water in the mixed solvent is not more than 60% by weight.

3. The method of claim 1 wherein the cellulosic polymer is at least one member selected from the group consisting of hydroxypropylmethyl cellulose phthalate, hydroxypropylmethyl cellulose acetate succinate, cellulose acetate phthalate, cellulose acetate trimellitate, carboxymethylethyl cellulose and ethyl cellulose.

* * * * *